United States Patent [19]

Belanger et al.

[11] Patent Number: 4,820,867

[45] Date of Patent: Apr. 11, 1989

[54] PHENOXYPROPOXY HALOPHENYLACETIC ACIDS AS LEUKOTRIENE ANTAGONISTS

[75] Inventors: Patrice Belanger, Dollard des Ormeaux; Rejean Fortin, Montreal; Yvan Guindon, Quebec; Christiane Yoakim, Montreal; Joshua Rokach, Laval, all of Canada

[73] Assignee: Merck Frosst Canada, Inc., Quebec, Canada

[21] Appl. No.: 855,051

[22] Filed: Apr. 22, 1986

Related U.S. Application Data

[63] Continuation of Ser. No. 591,344, Mar. 19, 1984, abandoned, which is a continuation-in-part of Ser. No. 487,434, Apr. 21, 1983, abandoned.

[51] Int. Cl.$^4$ .............................................. C07C 65/01
[52] U.S. Cl. ................... 562/478; 548/134; 548/353; 564/99; 568/325
[58] Field of Search ................ 562/478; 548/134, 313; 564/99; 568/325

[56] References Cited

U.S. PATENT DOCUMENTS 3,899,513  8/1975  Warren et al. .............. 260/465 F X

FOREIGN PATENT DOCUMENTS 0028063   5/1981  European Pat. Off. .
0056172   7/1982  European Pat. Off. .
0061800  10/1982  European Pat. Off. .
0104885   4/1984  European Pat. Off. .
0106565   4/1984  European Pat. Off. .
2058785   4/1981  United Kingdom .

OTHER PUBLICATIONS

Bailey et al., Ann. Rpts., Med. Chem., 17, 203 (1982).

Primary Examiner—Anton H. Sutto
Attorney, Agent, or Firm—Gabriel Lopez; Hesna J. Pfeiffer

[57] ABSTRACT

Compounds of the formula:

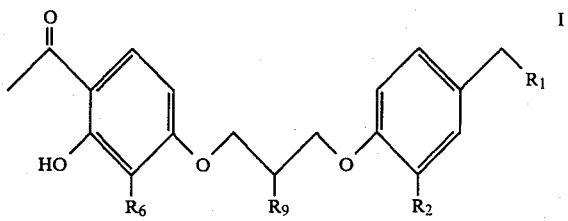

are antagonists of leukotrienes of $C_4$, $D_4$ and $E_4$, the slow reacting substance of anaphylaxis. These compounds are useful as anti-asthmatic, anti-allergic and anti-inflammatory agents.

9 Claims, No Drawings

PHENOXYPROPOXY HALOPHENYLACETIC ACIDS AS LEUKOTRIENE ANTAGONISTS

CROSS REFERENCE TO RELATED APPLICATION

This is a continuation of U.S. Ser. No. 591,344, filed Mar. 19, 1984, abandoned, which is a continuation-in-part of U.S. Ser. No. 487,434, filed Apr. 21, 1983, abandoned.

BACKGROUND OF THE INVENTION

Although the chemical identity of leukotrienes was not discovered until 1979, their history actually began in Australia in 1938 when researchers discovered slow reacting substances (SRS) which caused slow contractions of smooth muscle. When their chemical identity was learned, SRS was found to be a mixture of three previously unknown substances which are related chemically to the prostaglandins and thromboxanes. They were named leukotrienes because they are made by leukocytes and have three conjugated double bonds. Leukotrienes have major effects on the smaller peripheral airways of the lungs and on the larger central passages which include the trachea and the bronchi. In the presence of an allergy trigger, like pollen or dust, leukotrienes are manufactured from fatty substances trapped in the membrane of a triggered cell. A series of reactions within the cell generates a set of different leukotrienes which are transported through the cell membrane into the blood. Then they bring about a constriction of the air passages leading to breachlessness. In addition, the leukotrienes have been implicated as mediators of numerous other disease states, including inflammation, skin diseases and allergic reactions, among others. See, for example; D. M. Bailey et al., *Ann. Rpts. Med. Chem.* 17 203 (1982).

Several classes of compounds are known to be leukotriene antagonists. See for example: Great Britain Patent Specification No. 2,058,785 disclosing phenoxyalkoxyphenyl compounds which are useful as antagonists of the slow reacting substance of anaphylaxis; European patent application No. 56,172 disclosing phenoxy and thiophenoxy compounds which are useful as antagonists of the slow reacting substance of anaphylaxis; European patent application No. 61,800 disclosing anti-SRS-A bicyclic carboxylic acid derivatives.

OBJECTS OF THE INVENTION

It is an object of the present invention to provide compounds that act as antagonists to prevent leukotriene action or as inhibitors to prevent synthesis. A further object is to provide compounds which prevent or reverse leukotriene action or prevent leukotriene synthesis when administered orally. Yet another object is to provide compounds which prevent or reverse leukotriene action or prevent leukotriene synthesis when administered by insufflation, intravenously, rectally, topically, parenterally including subcutaneously and intramuscularly, or nasally. Another object is to provide methods for the preparation of these compounds. A further object is to provide intermediates useful in the synthesis of these compounds. Still another object is to provide pharmaceutical formulations for administering these compounds. These and other objects of the present invention will be apparent from the following description.

DETAILED DESCRIPTION

The present invention relates to compounds having activity as leukotriene antagonists, to methods for their preparation, to intermediates useful in their preparation and to methods for using these compounds. Because of their activity as leukotriene antagonists, the compounds of the present invention are useful as anti-asthmatic, anti-allergic, and anti-inflammatory agents and are useful in treating asthma, allergic rhinitis and chronic bronchitis and for amelioration of skin diseases like psoriasis and atopic exzema. These compounds are also useful to antagonize or inhibit the properties of leukotrienes relating to cardiovascular and vascular problems.

The compounds of the present invention have the formula:

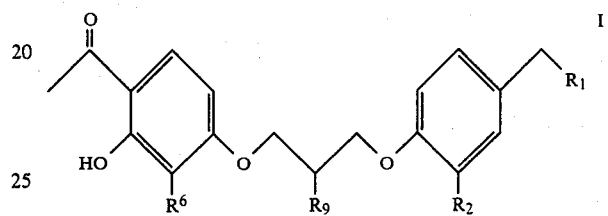

wherein
$R_1$ is $COOR_3$, $CH_2OH$; $CHO$; tetrazole; $CH_2NHSO_2R_4$; $CN$; $CON(R_5)_2$; a monocyclic or bicyclic heterocyclic ring containing an acidic hydroxyl group; or

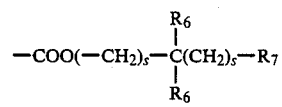

wherein
each s is independently 0–3;
$R_7$ is
  (A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
  (B) the radical $X$-$R_8$ wherein X is O, S or NH and $R_8$ contains up to 21 carbon atoms which may be straight chain or branched and is (1) a hydrocarbon radical or (2) an acyl radical of an organic acyclic or monocyclic carboxylic acid containing not more than 1 heteroatom selected from N, O or S in the ring;
$R_6$ is independently H or alkyl of 1 to 4 carbons which may be straight chain or branched;
$R_3$ is H or alkyl of 1 to 6 carbon atoms which may be straight chain, branched or cyclic;
$R_2$ is halogen (fluoride, chloride, bromide, iodide);
$R_4$ is OH; alkyl or alkoxy of 1 to 6 carbon atoms; phenyl or phenyl substituted by alkyl or alkoxy groups of 1 to 3 carbon atoms, halogen, hydroxy, haloalkyl, COOH, CN, formyl, acyl of 1 to 6 carbon atoms; or perfluoroalkyl of 1 to 4 carbon atoms;
$R_5$ is independently H, OH or alkyl of 1 to 4 carbons which may be straight chain or branched;

$R_9$ is hydrogen or hydroxyl; and pharmaceutically acceptable salts or acid addition salts thereof.

When $R_9$ is OH, this invention also embodies the racemic compounds formed, as well as the corresponding individual (R) and (S) isomers.

A preferred embodiment of the present invention relates to compounds of the Formula I wherein $R_1$ is $COOR_3$, $R_6$ is alkyl of 1 to 4 carbons which may be straight chain or branched and $R_3$ and the remaining substituents are as defined for structure I.

The compounds of the present invention may be prepared by reacting a compound of the formula II or III

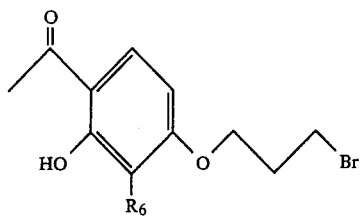

II or

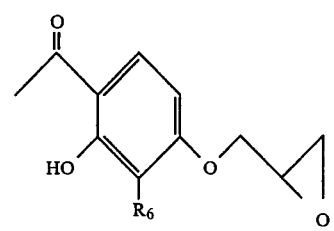

III with a compound of formula IV

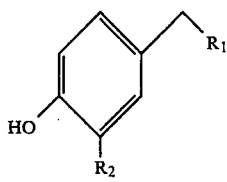

IV

The reaction takes place by refluxing a mixture of the compounds of formulas IV and II or III in an inert solvent such as, for example, methylethylketone (MEK), acetone, tetrahydrofuran (THF), triglyme or dichloromethane in the presence of a base. The reflux temperature is preferably in the range of from about 40° to about 130° C. The base may be an alkali metal carbonate, for example, $Li_2CO_3$, $Na_2CO_3$, $CsCO_3$ or $K_2CO_3$.

An alternate procedure involves reacting a compound of formulas V or VI prepared by reacting a compound of formula IV with 1,3-dibromopane or an epihalohydrin under the same conditions as described above, with a compound of formula VII, under the same conditions as above.

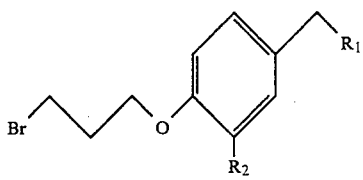

V or

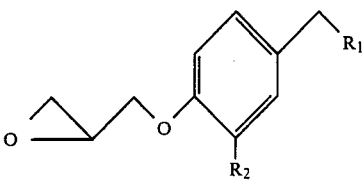

VI

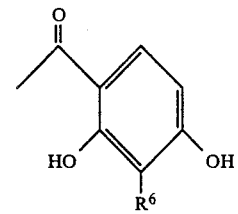

VII

Treatment of the compound of formula I ($R_1$=COOH) with borane in THF under known conditions (0° inert atmosphere) gives the corresponding alcohol, $R_1$=$CH_2OH$. Alternatively, borane reduction of a compound of formulas IV, V or VI under the same conditions gives the corresponding alcohols (IV, V, VI, $R_1$=$CH_2OH$) which are then converted following procedures described above to a compound of formula I ($R_1$=$CH_2OH$).

Oxidation of the alcohol of formula I ($R_1$=$CH_2OH$) by chromium trioxide in pyridine gives the corresponding aldehyde ($R_1$=CHO).

Reacting a compound of formula I ($R_1$=COOH) with the appropriate alkanol under acid catalysis yields the corresponding ester of formula I ($R_3$=alkyl).

Reacting the ester of formula I ($R_3$=alkyl) with ammonia, hydroxyl amine or alkyl- or dialkylamines in a suitable solvent such as THF yields the corresponding compound of formula I ($R_5$=H, OH or alkyl).

Dehydrating the amide of a compound of formula I ($R_5$=H) by treatment with phosphorus pentoxide yields the corresponding nitrile of formula I ($R_1$=CN).

Reacting the foregoing nitrile with sodium azide and $NH_4Cl$ in DMF gives the compound of formula I ($R_1$=tetrazole).

Treating the compound of formula I ($R_1$=$CH_2OH$) with triphenylphosphine and $CBr_4$ in an inert solvent such as diethylether gives the corresponding compound of formula I ($R_1$=$CH_2Br$) which in turn by treatment with excess $NH_3$ gives the compound of formula I ($R_1$=$CH_2NH_2$).

Treating the foregoing amine with a compound of $R_4SO_2Cl$ in a basic solvent such as pyridine gives the compound of formula I ($R_1$=$R_4SO_2NHCH_2$).

Pro-drug esters wherein $R_1$ is a monocyclic or bicyclic heterocyclic ring containing an acidic hydroxyl group are obtained by reacting the foregoing heterocycle with a compound of formula I ($R_1$=COOH) in the presence of dicyclohexylcarbodiimide and hydroxybenzotriazole in an inert solvent such as DMF.

Pro-drug esters wherein $R_1$ is

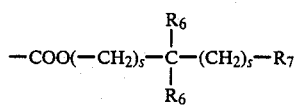

are obtained by reacting the sodium salt of I ($R_1$=COONa) with

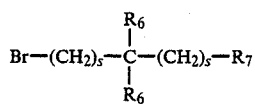

in an inert solvent such as DMF.

Pharmaceutically acceptable salts of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, tri-methylamine, diethanolamine, diethylamine, triethylamine, tripropylamine, ethanolamine, 2-dimethylaminoethanol, 2-diethylaminoethanol, tomethamine, lysine, arginine, histidine, caffeine, procaine, hydrabamine, choline, imidazole, betaine, ethylenediamine, glucosamine, methylglucamine, theobromine, purines, piperazine, N,N'-dibenzylethylenediamine, piperidine, N-ethylpiperidine, morpholine, N-ethylmorpholine, polyamine resins and the like.

Biological Activity

The compounds of formula I and pharmaceutically acceptable derivatives are therapeutically useful, since they antagonize in vitro and in vivo actions of leukotriene $D_4$ (a synthetic component of SRS). Thus these products will be useful in the treatment of pathological states in which leukotriene $D_4$ and related products are involved. This includes asthma and other allergic disease states, hypersensitivity (inflammation) reactions in skin, lung, gastrointestinal tract, cardiovascular disorders such as angina, etc. as well as other disorders where leukotriene actions are detrimental.

The antagonist activity of the compounds of the present invention was determined by measuring their ability to inhibit leukotriene $D_4$ induced bronchoconstriction in anaesthetized guinea pigs (modified Konzett-Rossler). When administrated directly into the duodenum (oral activity) they are active at 2.5–5 mg/kg. Oral activity is defined as the dose producing 50% inhibition when given 10 minutes before $LTD_4$. Percent inhibition was determined at 10 minutes and also at 30 and 50 minutes after antagonist administration. The time interval between $LTD_4$ administration was kept constant at 20 minutes in all experiments.

Table I is a comparison between three known leukotriene antagonists (entries 1, 2 and 3, see: G.B. Pat. No. 2,058,785, supra) and several compounds of the present invention (4–9). The median effective dose ($ED_{50}$ in mg/kg) required for the compounds of the present invention is either equal to or less than that of the prior art compounds. The percentage of bronchoconstriction inhibition of the compounds of the present invention, combined with the effective dose, demonstrates the superiority of the compounds of the present invention over the analogous prior art compounds.

TABLE I

Comparison of Compounds of the Present Invention With Known Compounds in Inhibiting Bronchoconstriction

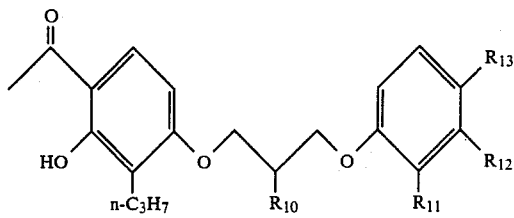

| Entry | $R_{10}$ | $R_{11}$ | $R_{12}$ | $R_{13}$ | $ED_{50}$ | % Inhibition After 30 Min. |
|---|---|---|---|---|---|---|
| 1 | H | H | H | COOH | 10 | 59 |
| 2 | H | H | $(CH_2)_2COOH$ | H | 10 | 32 |
| 3 | H | H | H | $CH=CHCO_2H$ | 20 | 56 |
| 4* | H | F | H | $CH_2COOH$ | 10 | 100 |
| 5* | OH | F | H | $CH_2COOH$ | 2.5 | 50 |
| 6* | OH | Br | H | $CH_2COOH$ | 2.5 | 35 |
| 7* | OH | Cl | H | $CH_2COOH$ | 10 | 63 |
| 8* | H | Cl | H | $CH_2COOH$ | 5 | 60 |
| 9* | H | Br | H | $CH_2COOH$ | 10 | 87 |

*Compounds of the present invention.

The magnitude of a prophylactic or therapeutic dose of a compound of formula I will, of course, vary with the nature of the severity of the condition to be treated and with the particular compound of formula I and its route of administration. In general, the daily dose range lies within the range of from about 0.2 mg to about 100 mg per kg body weight of a mammal.

The pharmaceutical compositions of the present invention comprise a compound of formula I or a pharmaceutically acceptable salt thereof as an active ingredient, and may also contain a pharmaceutically acceptable carrier and optionally other therapeutic ingredients.

The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The compositions include compositions suitable for oral, rectal, ophthalmic, pulmonary, nasal, dermal, topical or parenteral (including subcutaneous, intramuscular and intra-venous) administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range is from about 0.2 to about 20 mg (preferably from about 1 to about 10 mg) of a compound of formula I per kg of body weight per day and in the case where an oral composition is employed a suitable dosage range is, e.g. from about 1 to about 100 mg of a compound of formula I per kg of body weight per day, preferably from about 5 to about 40 mg/kg.

For administration by inhalation, the compounds of the present invention are conveniently delivered in the form of an aerosol spray presentation from pressurized packs or a nebuliser. The preferred composition for inhalation is a powder which may be formulated as a cartridge from which the powder composition may be inhaled with the aid of a suitable device. In the case of a pressurized aerosol, the dosage unit may be determined by providing a valve to deliver a metered amount.

Pharmaceutical compositions of the present invention suitable for oral administration and by inhalation in the case of asthma therapy may be presented as discrete units such as capsules, cachets or tablets each containing a predetermined amount of the active ingredient, as a powder or granules, or as a soluton or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Desirably, each tablet contains from about 25 mg to about 500 mg of the active ingredient and each cachet or capsule contains from about 25 to about 500 mg of the active ingredient.

In addition to the compounds of the Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ r —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

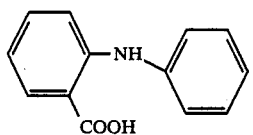

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

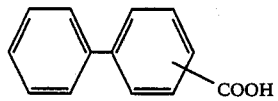

which can bear a variety of substituents and in which the free —COOH group can be in th form of a pharmaceutically acceptable salt group, e.g., —COO$^-$Na$^+$.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

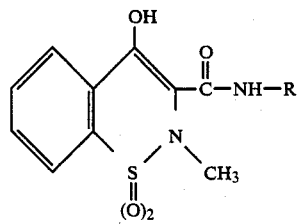

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3, ITC1, ITF, ITF182, KB1043, KC8973, KCNTEI6090, KME4, LA2851, LT696, LU20884, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent application Ser. No. 539,342, filed Oct. 5, 1983, Ser. No. 459,924, filed Jan. 21, 1983, Ser. No. 539,215, filed Oct. 5, 1983, and Ser. No. 547,161, filed Oct. 31, 1983, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983 which are hereby incorporated herein by reference and others known in the art such as those disclosed in European patent application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European patent application No. 11,067 or thromboxane antagonists such as those disclosed in U.S. Pat. No. 4,237,160. They may also contain histidine decarboxase inhibitors such as α-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP Pat. No. 40,696 and like compounds, such as those disclosed in U.S. Pat. Nos. 4,283,408; 4,362,736; and 4,394,508. The patent pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The following examples illustrate the present invention without, however, limiting the same thereto.

EXAMPLE 1

4-(3-(4-Acetyl-3-hydroxy-2-propylphenoxy)-2-hydroxypropoxy)-3-fluorobenzene acetic acid Step A: Preparation of 4-(3-(4-acetyl-3-hydroxypropyl-2-phenoxy)-2-hydroxypropoxy)-3-fluorobenzene acetic acid methyl ester A mixture of 4-(2,3-epoxypropoxy)-3-propyl-2-hydroxyacetophenone (1.25 g, 5 mmoles) and 3-fluoro-4-hydroxybenzene acetic acid methyl ester (0.92 g, 5 mmoles) and potassium carbonate (1.38 g, 10 mmoles) in methyl ethyl ketone (25 ml) was heated under reflux for 48 hours.

The reaction mixture was filtered, the solid was washed with acetone and the filtrate was evaporated to dryness. The residue was then chromatographed on silica gel to yield, on eluting with 20% EtOAc/hexane, 1.3 g of the title compound.

Elemental Analysis, Calc'd: C, 63.58; H, 6.26; F, 4.37; Obtained: C, 63.51; H, 6.20; F, 4.24.

Step B: Preparation of 4-(3-(4-acetyl-3-hydroxy-2-propylpropoxy)-3-fluorobenzene acetic acid The ester prepared in Step A, (1.1 g, 2.53 mmoles) dissolved in methanol (25 ml) containing 10N sodium hydroxide (1 ml) was refluxed gently for 15 minutes. The volatiles were removed in vacuo and the residue was taken up in water (50 ml). The solution was acidified with 20% citric acid and the mixture was extracted with EtOAc. The extracts were washed with brine, dried ($Na_2SO_4$) and concentrated in vacuo to yield 0.9 g of the title compound, m.p. 137°–138° C.

Elemental Analysis, Calc'd: C, 62,84; H, 5.99; F, 4.52; Obtained: C, 62.73; H, 5.91; F, 4.70.

EXAMPLE 2

4-(3-(4-Acetyl-3-hydroxy-2-propylphenoxy)-2-hydroxypropoxy)-3-chlorobenzene acetic acid Step A: Preparation of 4-(3-(4-acetyl-3-hydroxy-2-propylphenoxy)-2-hydroxypropoxy)-3-chlorobenzene acetic acid methyl ester By following Step A of Example 1, but substituting 3-chloro-4-hydroxy benzene acetic methyl ester for 3-fluoro-4-hydroxy benzene acetic methyl ester, the title compound was obtained as an oil.

Elemental Analysis, Calc'd: C, 61.26; H, 6.04; Cl, 7.86; Obtained: C, 61.06; H, 6.15; Cl, 7.93.

Step B: Preparation of 4-(3-(4-acetyl-3-hydroxy-2-propylphenoxy)-2-hydroxypropoxy)-3-chlorobenzene acetic acid By following Step B of Example 1, but substituting the title compound of Step A of this Example for the title compound of Step A of Example 1, the title compound was obtained, as an oil.

Elemental Analysis, Calc'd: C, 60.48; H, 5.77; Cl, 8.12; Obtained: C, 60.38; H, 5.70; Cl, 8.11.

EXAMPLE 3

4-(3-(4-Acetyl-3-hydroxy-2-propylphenoxy)-2-hydroxypropoxy)-3-bromobenzene acetic acid Step A: Preparation of 4-(3-(4-acetyl-3-hydroxy-2-propylphenoxy)-2-hydroxypropoxy)-3-bromobenzene acetic acid methyl ester By following Step A of Example 1, but substituting 3-bromo-4-hydroxy benzene acetic methyl ester for 3-fluoro-4-hydroxy benzene acetic methyl ester, the title compound was obtained as an oil.

Elemental Analysis, Calc'd: C, 55.77; H, 5.49; Br, 16.13; Obtained: C, 55.61; H, 5.41; Br, 16.39.

Step B: Preparation of 4-(3-(4-acetyl-3-hydroxy-2-propylphenoxy)-2-hydroxypropoxy)-3-bromobenzene acetic acid By following Step B of Example 1, but substituting the title compound of Step A of this Example for the title compound of Step A of Example 1, the title compound was obtained, m.p. 84°–84° C.

Elemental Analysis, Calc'd: C, 54.90; H, 5.24; Br, 16.60; Obtained: C, 54.63; H, 5.01; Br, 16.93.

EXAMPLE 4

4-(3-(4-Acetyl-3-hydroxy-2-propylphenoxy)-propoxy)-3-fluorobenzene acetic acid

Step A: Preparation of 4-(3-(4-acetyl-3-hydroxy-2-propylphenoxy)-propoxy)-3-fluorobenzene acetic acid methyl ester By following Step A of Example 1, but substituting 4-(3-bromopropoxy)-3-propyl-2-hydroxy acetophenone for 4-(2,3-epoxypropoxy)-3-propyl-2-hydroxy acetophenone, the title compound was obtained as an oil.

Elemental Analysis, Calc'd: C, 65.70; H, 6.23; F, 4.52; Obtained: C, 65.76; H, 6.06; F, 4.63.

Step B: Preparation of 4-(3-(4-acetyl-3-hydroxy-2-propylphenoxy)-propoxy)-3-fluorobenzene acetic acid By following Step B of Example 1, but substituting the title compound of Step A of this Example for the title compound of Step A of Example 1, the title compound was obtained, m.p. 121°–123° C.

Elemental Analysis, Calc'd: C, 65.33; H, 6.23; F, 4.70; Obtained: C, 65.49; H, 6.32; F, 4.50.

EXAMPLE 5

4-(3-(4-Acetyl-3-hydroxy-2-propylphenoxy)-2-propoxy)-3-chlorobenzene acetic

Step A: Preparation of 4-(3-(4-acetyl-3-hydroxy-2-propylphenoxy)-2-propoxy)-3-chlorobenzene acetic methyl ester By following Step A of Example 4, but substituting 3-chloro-4-hydroxy benzene acetic methyl ester for 3-fluoro-4-hydroxy benzene acetic methyl ester, the title compound was obtained as an oil.

Elemental Analysis, Calc'd: C, 63.51; H, 6.26; Cl, 8.15; Obtained: C, 63.78; H, 6.62; Cl, 8.37.

Step B: Preparation of 4-(3-(4-acetyl-3-hydroxy-2-propylphenoxy)propoxy)-3-chlorobenzene acetic By following Step B of Example 1, but substituting the title compound of Step A of this Example for the title compound of Step A of Example 1, the title compound was obtained, m.p. 110°–111° C.

Elemental Analysis, Calc'd: C, 62.78; H, 5.99; Cl, 8.42; Obtained: C, 62.60; H, 6.32; Cl, 8.37.

EXAMPLE 6

4-(3-(4-Acetyl-3-hydroxy-2-propylphenoxy)-propoxy)-3-bromobenzene acetic acid

Step A: Preparation of 4-(3-(4-acetyl-3-hydroxy-2-propylphenoxy)-propoxy)-3-bromobenzene acetic acid methyl ester By following Step A of Example 4, but substituting 3-bromo-4-hydroxy benzene acetic methyl ester for 3-fluoro-4-hydroxy benzene acetic methyl ester, the title compound was obtained, m.p. 91°–92°.

Elemental Analysis, Calc'd: C, 57.63; H, 5.68; Br, 16.67. Obtained: C, 57.35; H, 5.72; Br, 16.35.

Step B: Preparation of 4-(3-(4-acetyl-3-hydroxy-2-propylphenoxy)-propoxy)-3-bromobenzene acetic acid By following Step B of Example 1, but substituting the title compound of Step A of this Example for the title compound of Step A of Example 1, the title compound was obtained, m.p. 111°–112° C.

Elemental Analysis, Calc'd: C, 56.78; H, 5.42; Br, 17.17; Obtained: C, 56.82; H, 5.34; Br, 17.22.

EXAMPLE 7

Following the general procedures described hereinabove, the following compounds are prepared:

4-(3-(4-Acetyl-3-hydroxy-2-propylphenoxy-2-hydroxypropoxy)-3-fluorobenzene acetic acid ethyl ester;

4-(3-(4-Acetyl-3-hydroxy-2-propylphenoxy-2-hydroxypropoxy)-3-fluorobenzenethanol;

4-(3-(4-Acetyl-3-hydroxy-2-propylphenoxy-2-hydroxypropoxy)-3-fluorobenzeneacetaldehyde;

4-(3-(4-Acetyl-3-hydroxy-2-propylphenoxy-2-hydroxypropoxy)-3-fluorobenzenemethyltetrazole;

4-(3-(4-Acetyl-3-hydroxy-2-propylphenoxy-2-hydroxypropoxy)-3-fluorobenzeneethylamine;

N-Methylsulfonyl-4-(3-(4-acetyl-3-hydroxy-2-propylphenoxy-2-hydroxypropoxy)-3-fluorobenzeneethylamine;

4-(3-(4-Acetyl-3-hydroxy-2-propylphenoxy-2-hydroxypropoxy)-3-fluorobenzylnitrile;

N,N-Dimethyl-4-(3-(4-acetyl-3-hydroxy-2-propylphenoxy-2-hydroxypropoxy)-3-fluorobenzeneacetamide;

4-(3-(4-Acetyl-3-hydroxy-2-propylphenoxy-2-hydroxypropoxy)-3-fluorobenzene acetic acid, 4-methoxy-1,2,5-thiadiazol-3-yl-ester.

What is claimed is:

1. Compounds having the formula:

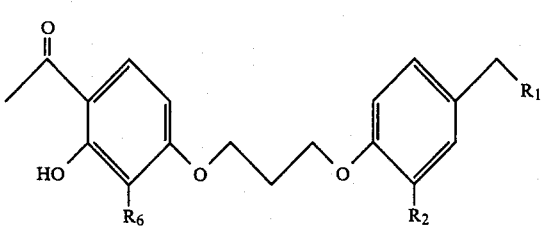

wherein
$R_1$ is $COOR_3$; $CH_2OH$; $CHO$; or $CH_2NHSO_2R_4$;
$R_2$ is fluoride or bromide;
$R_3$ is H or alkyl of 1 to 6 carbon atoms which may be straight chain, branched or cyclic;
$R_4$ is OH; alkyl, or alkoxy of 1 to 6 carbon atoms; phenyl or phenyl substituted by alkyl or alkoxy groups of 1 to 3 carbon atoms, halogen, hydroxy, haloalkyl, COOH, CN, formyl, acyl of 1 to 6 carbon atoms; or perfluoroalkyl of 1 to 4 carbon atoms;
$R_6$ is independently H or alkyl of 1 to 4 carbons;
and pharmaceutically acceptable salts or acid addition salts thereof.

2. Compounds having the formula:

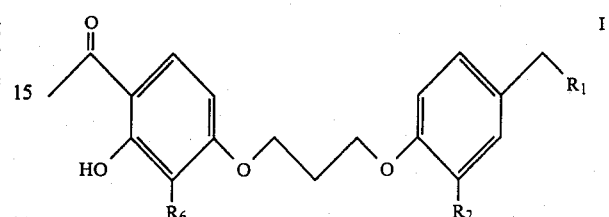

wherein
$R_1$ is $COOR_3$; $CH_2OH$; $CHO$; tetrazole; $CH_2NHSO_2R_4$; a monocyclic or bicyclic heterocyclic ring containing an acidic hydroxyl group; or

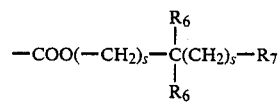

wherein
each s is independently 0–3;
$R_7$ is
(A) a monocyclic or bicyclic heterocyclic radical containing from 3 to 12 nuclear carbon atoms and 1 or 2 nuclear heteroatoms selected from N and S with at least one being N, and with each ring in the heterocyclic radical being formed of 5 or 6 atoms, or
(B) the radical $X-R_8$ wherein X is O, S or NH and $R_8$ contains up to 21 carbon atoms and is (1) a hydrocarbon radical or (2) an acyl radical of an organic acyclic or monocyclic carboxylic acid containing not more than 1 heteroatom in the ring;
$R_6$ is independently H or alkyl of 1 to 4 carbons;
$R_3$ is H or alkyl of 1 to 6 carbon atoms which may be straight chain, branched or cyclic;
$R_2$ is fluoride or bromide;
$R_4$ is OH; alkyl, or alkoxy of 1 to 6 carbon atoms; phenyl or phenyl substituted by alkyl or alkoxy groups of 1 to 3 carbon atoms, halogen, hydroxy, haloalkyl, COOH, CN, formyl, acyl of 1 to 6 carbon atoms; or perfluoroalkyl of 1 to 4 carbon atoms;
$R_5$ is independently H, OH or alkyl of 1 to 4 carbons;
and pharmaceutically acceptable salts or acid addition salts thereof.

3. The compounds of claim 2 wherein $R^7$ is $X-R^8$ and X is S.

4. The compounds of claim 2 wherein $R^7$ is $X-R^8$ and X is O.

5. The compounds of claim 2 wherein $R^7$ is $X-R^8$ and X is NH.

6. A compound of claim 2 which is:
4-(3-(4-Acetyl-3-hydroxy-2-propylphenoxy)-propoxy-3-fluorobenzene acetic acid;

4-(3-(4-Acetyl-3-hydroxy-2-propylphenoxy)-propoxy)-3-bromobenzene acetic acid; or N-Methylsulfonyl-4-(3-(4-acetyl-3-hydroxy-2-propylphenoxy)-2-hydroxypropoxy)-3-fluorobenzeneethylamine.

7. A composition containing a compound of claim 2 and a pharmaceutically acceptable carrier.

8. A compound of claim 2 wherein $R_2$ is fluoride.

9. A compound of claim 2 which is:
4-(3-(4-Acetyl-3-hydroxy-2-propylphenoxy)propoxy)-3-fluorobenzene acetic acid;
4-(3-(4-Acetyl-3-hydroxy-2-propylphenoxy)propoxy)-3-bromobenzene acetic acid.

* * * * *